(12) United States Patent
Patel

(10) Patent No.: US 11,633,178 B2
(45) Date of Patent: Apr. 25, 2023

(54) HAND GRIP SYSTEM FOR SURGICAL RETRACTOR

(71) Applicant: Jiffy Knee, LLC, Suffolk, VA (US)

(72) Inventor: Manish A. Patel, Suffolk, VA (US)

(73) Assignee: JIFFY KNEE, LLC, Suffolk, VA (US)

( * ) Notice: Subject to any disclaimer, the term of this patent is extended or adjusted under 35 U.S.C. 154(b) by 0 days.

(21) Appl. No.: 17/579,668

(22) Filed: Jan. 20, 2022

(65) Prior Publication Data

US 2022/0249079 A1  Aug. 11, 2022

Related U.S. Application Data

(60) Provisional application No. 63/147,783, filed on Feb. 10, 2021.

(51) Int. Cl.
*A61B 17/02* (2006.01)
*A61B 17/00* (2006.01)

(52) U.S. Cl.
CPC ...... *A61B 17/02* (2013.01); *A61B 2017/0046* (2013.01)

(58) Field of Classification Search
CPC ............ A61B 17/02; A61B 2017/0046; A61B 2017/00424; A61B 2017/0042; A61B 2017/0268; Y10T 403/475
USPC ......................................................... 600/226
See application file for complete search history.

(56) References Cited

U.S. PATENT DOCUMENTS

| | | | | |
|---|---|---|---|---|
| 1,728,619 A | * | 9/1929 | Lambert | ............ B26B 3/00 81/177.1 |
| D531,310 S | * | 10/2006 | Wolter | ............ D24/133 |
| 2016/0184046 A1 | * | 6/2016 | Blain | ............ A61B 17/1659 600/249 |
| 2017/0303905 A1 | * | 10/2017 | Wilson | ............ A61B 17/02 |
| 2019/0216186 A1 | * | 7/2019 | Shintani | ............ B25G 1/102 |
| 2021/0007862 A1 | * | 1/2021 | Finley | ............ A61B 17/00 |

* cited by examiner

*Primary Examiner* — Julianna N Harvey
*Assistant Examiner* — Angel Roberto Mora-Velazquez
(74) *Attorney, Agent, or Firm* — Peter J Van Bergen

(57) ABSTRACT

A hand grip system for a surgical retractor includes a grip region of a rigid surgical retractor tool having at least two holes passing there through. The hand grip system also includes a monolithic hand grip encasing the grip region and filling the holes. The monolithic hand grip includes a first elongate region having a convex cylindrical shape adjoining a second elongate region having a concave cylindrical shape.

2 Claims, 2 Drawing Sheets

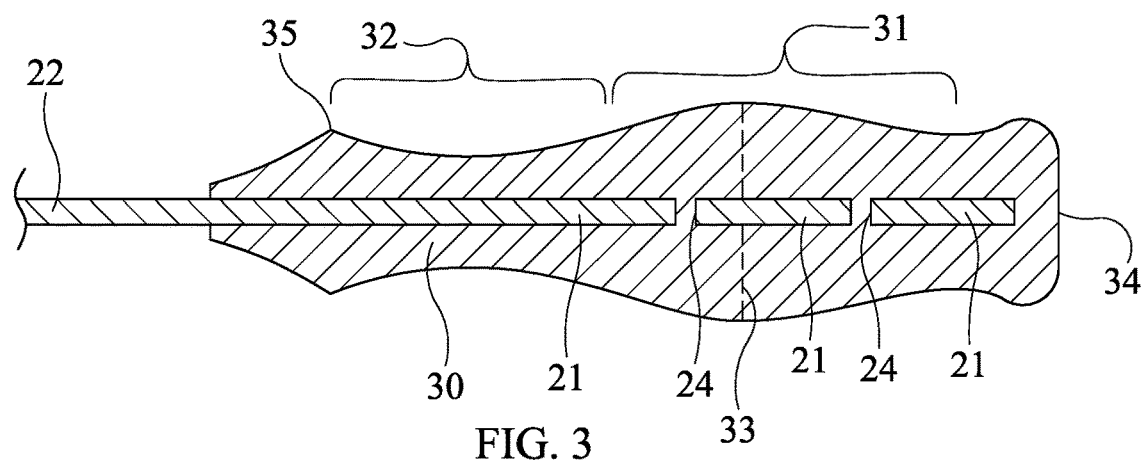
FIG. 3
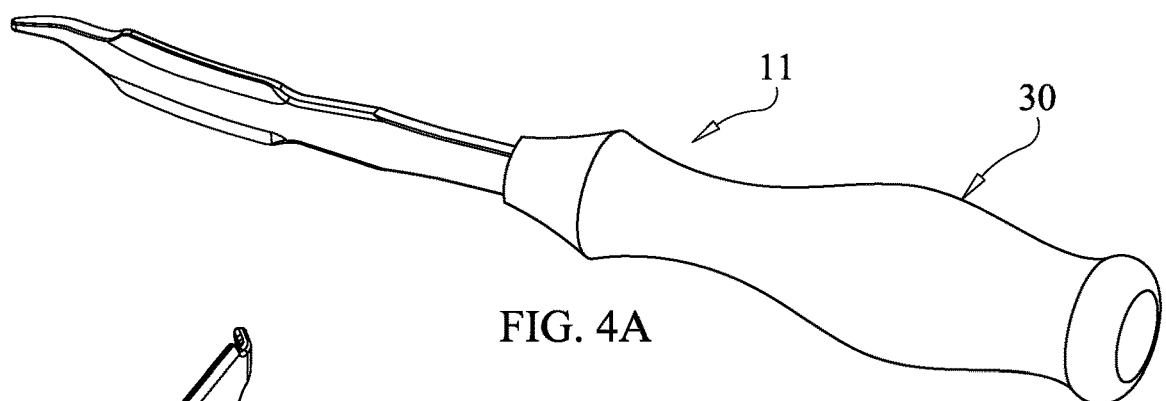
FIG. 4A
FIG. 4B
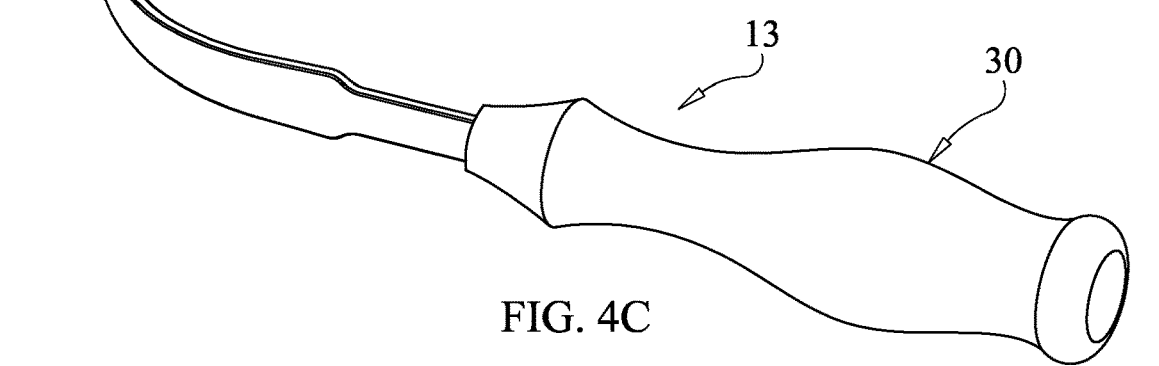
FIG. 4C

HAND GRIP SYSTEM FOR SURGICAL RETRACTOR

Pursuant to 35 U.S.C. § 119, the benefit of priority from provisional application 63/147,783, with a filing date of Feb. 10, 2021, is claimed for this non-provisional application.

FIELD OF THE INVENTION

The invention relates generally to surgical retractors, and more particularly to a hand grip system for surgical retractors such as those used in knee surgery.

BACKGROUND OF THE INVENTION

Retractors are tools used in almost all surgical procedures. In general, a retractor is used to pull skin, muscle, ligament, and/or tendon tissue away from an operative site to provide visual clarity and the space needed to perform a surgical procedure. Many retractors, such as those used during knee replacement surgery, require medical personnel to apply and maintain significant amounts of force to keep the operative site free of unwanted obstructions. For strength and simplicity, conventional retractors have a flat metal handle or grip region leading to a specifically-designed tool end that interfaces with tissue that is to be retracted. Unfortunately, the amount of force that one must apply to and maintain on the metal handle can quickly cause fatigue for medical personnel where such fatigue can negatively impact the efficacy and efficiency of a surgical procedure.

SUMMARY OF THE INVENTION

Accordingly, it is an object of the present invention to provide an improved hand grip system for a surgical retractor.

Another object of the present invention is to provide a hand grip system for a surgical retractor that efficiently transfers forces applied thereto.

Still another object of the present invention is to provide a hand grip system for a surgical retractor that reduces user fatigue during use thereof.

Other objects and advantages of the present invention will become more obvious hereinafter in the specification and drawings.

In accordance with the present invention, a hand grip system for a surgical retractor includes a grip region of a rigid surgical retractor tool. The grip region has at least two holes passing there through. The hand grip system also includes a monolithic hand grip encasing the grip region and filling the holes. The monolithic hand grip includes a first elongate region adjoining a second elongate region. The first elongate region has a convex cylindrical shape and the second elongate region has a concave cylindrical shape.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein:

FIG. 3 is a side cross-sectional view of the VMO muscle retractor's hand grip system in its fully fabricated form in accordance with an embodiment of the present invention;

FIG. 4A is a perspective view of a knee surgery's straight retractor incorporating the hand grip system of the present invention;

FIG. 4B is a perspective view of a knee surgery's collateral retractor incorporating the hand grip system of the present invention; and FIG. 4C is a perspective view of a knee surgery's posterior cruciate ligament (PCL) retractor incorporating the hand grip system of the present invention.

DETAILED DESCRIPTION OF THE INVENTION

Figure 1:
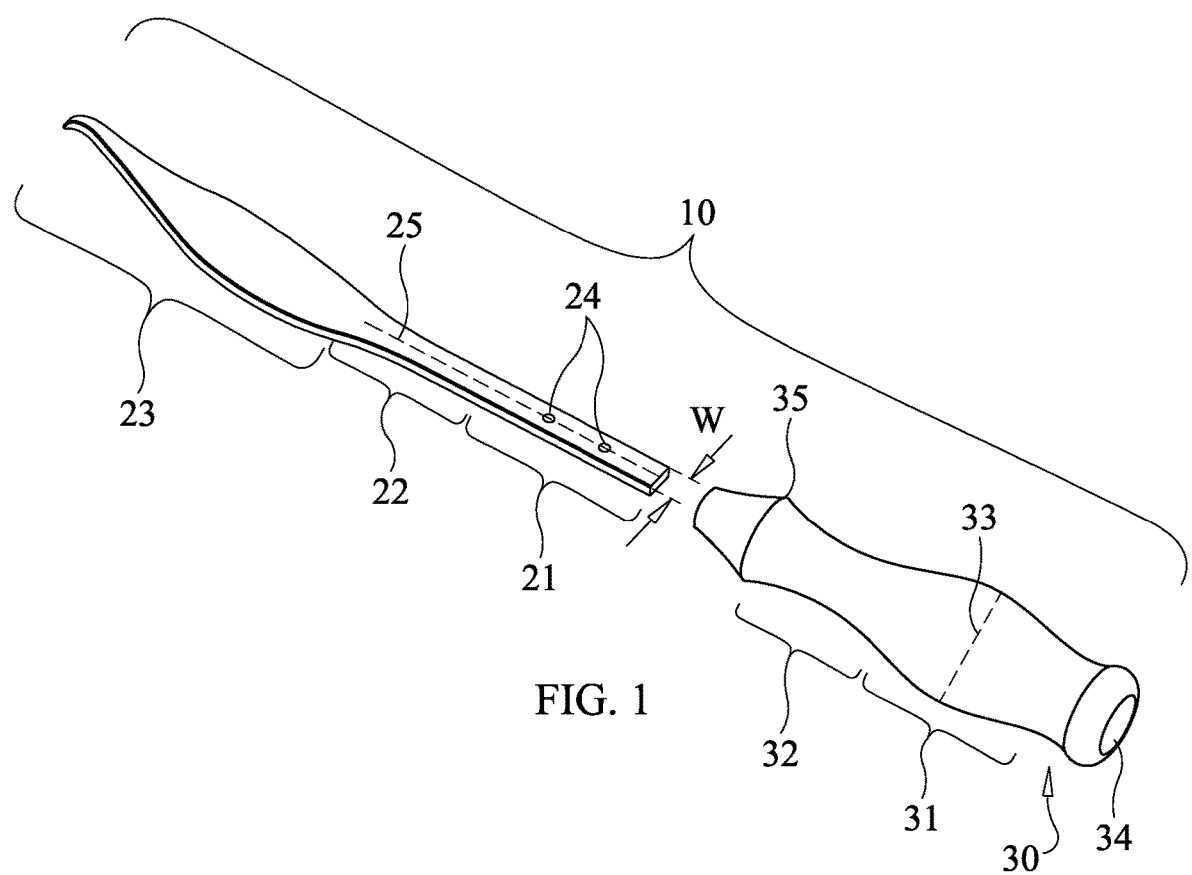
FIG. 1 is an exploded view of a knee surgery's vastus medialis oblique (VMO) muscle retractor having a hand grip system in accordance with an embodiment of the present invention.

Referring now to the drawings, simultaneous reference will be made to FIGS. 1-3 where a knee surgery's vastus medialis oblique (VMO) muscle retractor having a hand grip system in accordance with an embodiment of the present invention is shown and is referenced generally by numeral 10. While VMO muscle retractors are known in the art of knee surgery, the present invention incorporates a novel hand grip system that helps to improve efficiency and efficacy of knee surgeries such as knee replacement surgery. Since knee replacement surgery typically employs several types of retractors, the novel hand grip system used for retractor 10 can be incorporated into each type of knee surgery retractor as will be explained further below. It is further to be understood that the present invention's novel hand grip system can be employed in retractors used for a variety of other surgical procedures without departing from the scope of the present invention.

Figure 2:
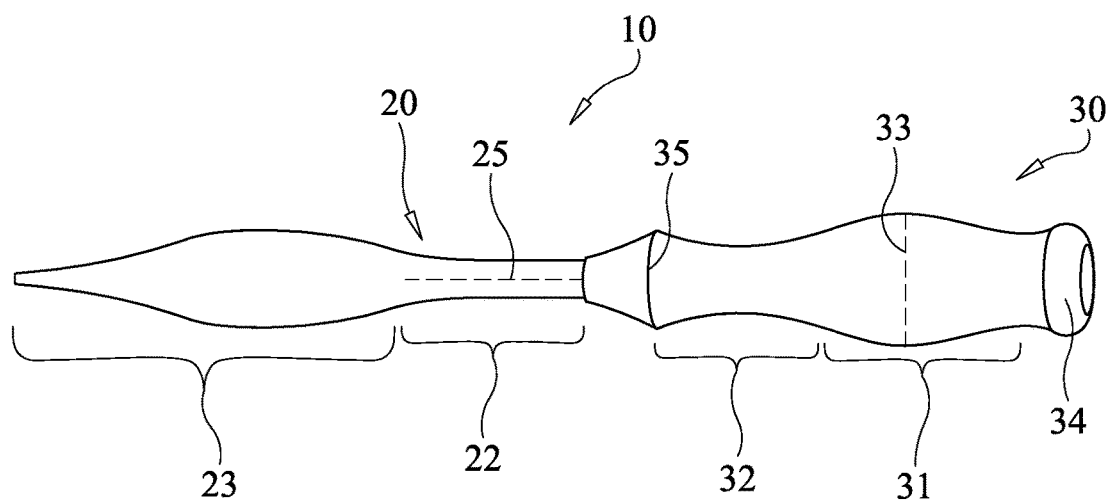
FIG. 2 is a plan view of the VMO muscle retractor illustrating the hand grip system in its fully fabricated form in accordance with an embodiment of the present invention.

Retractor 10 includes a tool 20 and a hand grip 30 that is permanently coupled to tool 20 to form the hand grip system of the present invention as shown in FIGS. 2 and 3. In general, the hand grip system of the present invention includes hand grip 30 molded directly onto a portion of tool 20. Accordingly, it is to be understood that the exploded view of retractor 10 shown in FIG. 1 is presented only for purposes of more clearly illustrating the features of tool 20 that will be encased by and contained within hand grip 30 following the molding of hand grip 30 onto tool 20.

Tool 20 is typically a monolithic element made from a rigid material suitable for use in surgical environments. Suitable materials for tool 20 include stainless steel or any other strong and rigid medical grade material. Tool 20 includes three serially arranged regions. More specifically, tool 20 has a grip region 21, a lever region 22 having a first end coupled to grip region 21, and a patient-engaging region 23 coupled to the second end of lever region 22. The primary novel features of tool 20 provided by the present invention reside in grip region 21. Lever region 22 is generally straight and is of a length that provides sufficient leverage for the retractor's intended use. Patient-engaging region 23 is configured for an intended surgical retraction where such configuration is not a limitation of the present invention. Indeed and as will be explained further below, the hand grip system of the present invention can be utilized for a variety of surgical retractors such as the multiple types of retractors used in knee replacement surgeries.

Grip region 21 is generally a flat rectangular plate region that provides the base and support for hand grip 30. Grip region 21 has at least two through holes 24 that allow the mold material (i.e., the material of hand grip 30) to pass there through. In some embodiments of the present invention, holes 24 are arranged in linear alignment with one another with each of holes 24 being centered on the center longitudinal axis 25 of grip region 21 as illustrated. The diameter of each hole 24 should not exceed approximately one-third of the width "W" of grip region 21. The locations of holes 24 relative to features of hand grip 30 will be explained further below.

As mentioned above, hand grip 30 is over-molded onto grip region 21 of tool 20 to thereby fully encase grip region 21. In general, material used for hand grip 30 can include a variety of thermoplastic polyurethanes (TPU) or thermoplastic elastomers (TPE). To provide the needed strength during use as will be described further below, the material selected for hand grip 30 will generally have durometer hardness in a range of 70 A to 90 A. During the molding process, the material used for hand grip 30 is extruded into holes 24 to thereby fill and extend through holes 24. The material of hand grip 30 filling holes 24 is contiguous with the hand grip material on opposing sides of grip region 21 as best illustrated in FIG. 3. Accordingly, hand grip 30 is a monolithic structure encasing and integrally coupled to grip region 21 such that the combination of hand grip 30 encasing grip region 21 forms the hand grip system of the present invention.

Hand grip 30 includes serially arranged and integrated palm/heel region 31 and finger wrap region 32. In general, palm/heel region 31 is an elongate and convex cylindrical portion of hand grip 30, while finger wrap region 32 is an elongate and concave cylindrical portion of hand grip 30. Palm/heel region 31 presents larger radial cross-sections taken along the length thereof as compared to the radial cross-sections of finger wrap region 32 taken along the length thereof. In some embodiments of the present invention, palm/heel region 31 terminates at one end thereof in a knob 34 that defines one end of retractor 10. Knob 34 has a circumferential profile that is greater than that of the adjoining portion of palm/heel region 31. Knob 34 serves as a stop for a user's hand to prevent slippage from hand grip 30 when a user applies a pulling force along the length of retractor 10. The concavity of finger wrap region 32 creates a lip 35 at the end of finger wrap region 32. As will be explained further below, lip 35 serves as a stop for a user's thumb when a user applies a pushing force along the length of retractor 10.

Holes 24 are positioned such that they will reside at least along palm/heel region 31 when grip region 21 of tool 20 is encased by hand grip 30. In some embodiments of the present invention, at least one hole 24 resides on each side of the largest diameter portion 33 of palm/heel region 31. In the illustrated embodiment, two holes 24 are used and are disposed on opposing sides of the largest diameter portion 33 of palm/heel region 31. In this way, both pushing and pulling forces (applied along central longitudinal axis 25 of tool 20 and on either side of largest diameter portion 33) are efficiently transferred to tool 20 thereby efficiently transferring a user's push/pull force to tool 20 and minimizing fatigue on the medical personnel using retractor 10.

In use, a surgeon or their assistant (hereinafter referred to simply as "user") grips retractor 10 via its hand grip 30. More specifically, the user places the heel of their hand along palm/heel region 31. If knob 34 is included in hand grip 30, the heel of the user's hand can rest against knob 34. The user wraps their pinky and ring fingers about palm/heel region 31. The user's thumb, index finger, and middle finger engage/wrap about finger wrap region 32 with the tip of the user's thumb resting near or against lip 35. Pushing or pulling forces applied by the user's hand along the length of retractor 10 are primarily passed to tool 20 via palm/heel region 31. By disposing holes 24 along region 31 as described above and using a relatively hard material for hand grip 30, the user-applied forces are efficiently transferred to tool 20 without compromising the integrity of hand grip 30. Further, the combination of the larger radial cross-sections of palm/heel region 31 and smaller radial cross-sections of finger wrap region 32 provide the user with a grip configuration that minimizes user fatigue thereby allowing the user to provide the requisite amount of retraction force for a longer period of time.

As mentioned above, the novel features of the hand grip system described herein can be incorporated into other types of typical knee surgery retractors. Three such retractor examples are illustrated in FIGS. 4A-4C where a straight retractor 11 (FIG. 4A), a collateral retractor 12 (FIG. 4B), and a PCL retractor 13 (FIG. 4C) are shown. Each of these retractors is constructed to have the novel hand grip system as described above.

The advantages of the present invention are numerous. The retractor's hand grip system is a novel grip-to-tool construction that provides for efficient transfer of forces while minimizing user fatigue. As a result, a variety of surgical procedures can be improved in terms of efficiency and efficacy.

Although the invention has been described relative to specific embodiments thereof, there are numerous variations and modifications that will be readily apparent to those skilled in the art in light of the above teachings. For example, additional holes could be provided in the retractor tool's grip region with the additional holes being disposed in the finger wrap portion of the hand grip. It is therefore to be understood that, within the scope of the appended claims, the invention may be practiced other than as specifically described.

What is claimed as new and desired to be secured by Letters Patent of the United States is:

1. A hand grip system for a surgical retractor, comprising:
    a grip region of a rigid surgical retractor tool, said grip region having at least two holes passing there through, each of said holes centered on a center longitudinal axis of said grip region, wherein a diameter of each of said holes does not exceed W/3 where "W" is a width of said grip region;
    a monolithic hand grip encasing said grip region and filling said holes, said monolithic hand grip selected from the group consisting of thermoplastic polyurethanes and thermoplastic elastomers having durometer hardness in the range of 70 A to 90 A, said monolithic hand grip including a serial arrangement of a knob, a first elongate region adjoining said knob, and a second elongate region adjoining said first elongate region,
    said first elongate region having a convex cylindrical shape,
    said second elongate region having a concave cylindrical shape, wherein radial cross-sections of said first elongate region are greater than radial cross-sections of said second elongate region;
    said knob having a circumferential profile greater than that of an adjoining portion of said first elongate region;
    said grip region extending through said first elongate region and said second elongate region; and
    said holes being disposed within said first elongate region and distributed on opposing sides of a largest diameter portion of said first elongate region, wherein forces applied to either of said opposing sides of said largest diameter of said first elongate region are transferred to said grip region along said center longitudinal axis by said monolithic rand grip.

2. A hand grip system as in claim 1, wherein said grip region is made from a medical grade material.

\* \* \* \* \*